US012592135B2

(12) United States Patent
Perez et al.

(10) Patent No.:    US 12,592,135 B2
(45) Date of Patent:        Mar. 31, 2026

(54) SYSTEM, DEVICE, AND METHOD FOR SMOKE DISCRIMINATION AND IDENTIFICATION OF FIRE SOURCE

(71) Applicant: Carrier Corporation, Palm Beach Gardens, FL (US)

(72) Inventors: Raul Perez, Esplugues de Llobregat (ES); Inigo Barrera, Hospitalet de Llobregat (ES); Ricard Burriel, Barcelona (ES); Jose Manuel Munuera, Ripollet (ES); Joan Radua, Barcelona (ES)

(73) Assignee: KIDDE FIRE PROTECTION, LLC, Bradenton, FL (US)

( * ) Notice: Subject to any disclaimer, the term of this patent is extended or adjusted under 35 U.S.C. 154(b) by 23 days.

(21) Appl. No.: 18/481,747

(22) Filed:     Oct. 5, 2023

(65)            Prior Publication Data

US 2024/0119818 A1     Apr. 11, 2024

(51) Int. Cl.
*G08B 17/10*         (2006.01)
*G01N 33/00*         (2006.01)
        (Continued)

(52) U.S. Cl.
CPC ......... *G08B 17/10* (2013.01); *G01N 33/0065* (2013.01); *G01N 33/0067* (2013.01);
        (Continued)

(58) Field of Classification Search
CPC .... G08B 17/10; G08B 17/117; G08B 29/188; G08B 29/183; G08B 21/14; G01N 33/0065; G01N 33/0067
See application file for complete search history.

(56)            References Cited

U.S. PATENT DOCUMENTS 5,592,147 A  *  1/1997  Wong .................. G08B 29/188
                                                340/522
6,111,512 A     8/2000  Sugimoto et al.
                (Continued)

FOREIGN PATENT DOCUMENTS

CN       111553403 A     8/2020
CN       111914606 A    11/2020
                (Continued)

OTHER PUBLICATIONS

European Search Report for Application No. 22382964.9, Issued Mar. 30, 2023, 16 Pages.

*Primary Examiner* — John A Tweel, Jr.
(74) *Attorney, Agent, or Firm* — CANTOR COLBURN LLP

(57)            ABSTRACT

A system for smoke/fire discrimination and identification of the fire source is provided. The system comprises a control unit that is configured to receive data pertaining to gases present in the smoke generated by a burning material and receive data pertaining to temporal characteristics of fire caused by the burning material. The control unit identifies the burning material based on the data pertaining to the one or more gas and the data pertaining to temporal characteristics of fire; and trigger a fire event based on the identified burning material. The control unit identifies and classifies the burning material as one of the known burning materials based on matching of the detected gas and the captured temporal characteristics with the database.

17 Claims, 8 Drawing Sheets

(51) Int. Cl.

| | |
|---|---|
| *G06F 16/903* | (2019.01) |
| *G08B 17/117* | (2006.01) |
| *G08B 21/14* | (2006.01) |
| *G08B 29/18* | (2006.01) |

(52) U.S. Cl.
CPC ...... *G06F 16/90335* (2019.01); *G08B 17/117* (2013.01); *G08B 21/14* (2013.01); *G08B 29/183* (2013.01); *G01N 33/0068* (2024.05)

(56) References Cited

U.S. PATENT DOCUMENTS

| | | | |
|---|---|---|---|
| 6,184,792 B1 | 2/2001 | Privalov et al. | |
| 6,937,743 B2 | 8/2005 | Rizzotti et al. | |
| 6,985,081 B2 * | 1/2006 | Wagner .................. | G08B 17/10 |
| | | | 73/863.31 |
| 7,286,704 B2 | 10/2007 | Pfefferseder et al. | |
| 7,680,297 B2 | 3/2010 | Privalov | |
| 7,701,362 B2 | 4/2010 | Philiben | |
| 7,710,280 B2 | 5/2010 | McLellan | |
| 7,872,584 B2 | 1/2011 | Chen | |
| 7,934,412 B2 | 5/2011 | Prince | |
| 8,240,215 B2 | 8/2012 | Holt et al. | |
| 8,462,980 B2 | 6/2013 | Caballero et al. | |
| 8,587,442 B2 | 11/2013 | Loepfe et al. | |
| 9,905,116 B2 | 2/2018 | Gruber et al. | |
| 9,928,709 B2 | 3/2018 | Takasu et al. | |
| 9,997,038 B2 | 6/2018 | Peters et al. | |
| 10,712,263 B2 | 7/2020 | Erdtmann | |
| 11,195,010 B2 | 12/2021 | Lapczynski et al. | |
| 11,232,690 B2 * | 1/2022 | Shepard ................. | G08B 25/08 |
| 11,340,097 B1 * | 5/2022 | Deutsch .............. | G08B 25/001 |
| 11,935,390 B2 * | 3/2024 | Munuera ............... | G08B 17/10 |
| 2015/0185194 A1 | 7/2015 | Prince et al. | |
| 2017/0169683 A1 * | 6/2017 | Ryder ................... | G01J 5/0846 |
| 2020/0064248 A1 * | 2/2020 | Houck ................. | G08B 17/117 |
| 2022/0157154 A1 | 5/2022 | Munuera | |
| 2022/0189272 A1 | 6/2022 | Hou et al. | |

FOREIGN PATENT DOCUMENTS

| | | |
|---|---|---|
| CN | 113963301 A | 1/2022 |
| CN | 111462451 B | 4/2022 |
| EP | 1687784 B1 | 1/2009 |
| EP | 1330800 B1 | 6/2012 |
| EP | 2571001 B1 | 4/2017 |
| EP | 3347883 B1 | 11/2020 |
| EP | 3948201 B1 | 3/2025 |
| WO | 2010088049 A1 | 8/2010 |
| WO | 2021115728 A1 | 6/2021 |

* cited by examiner

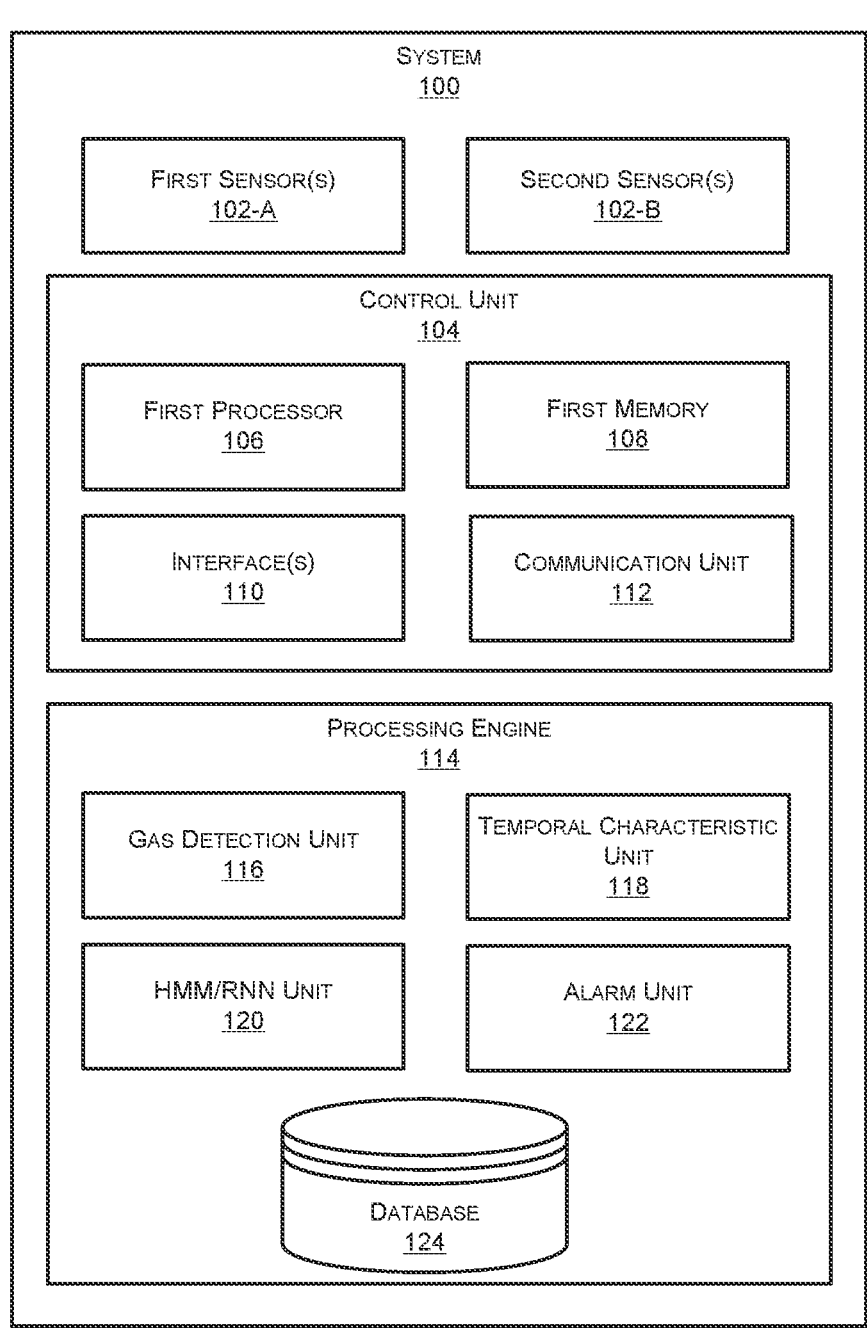
*FIG. 1*

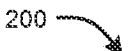
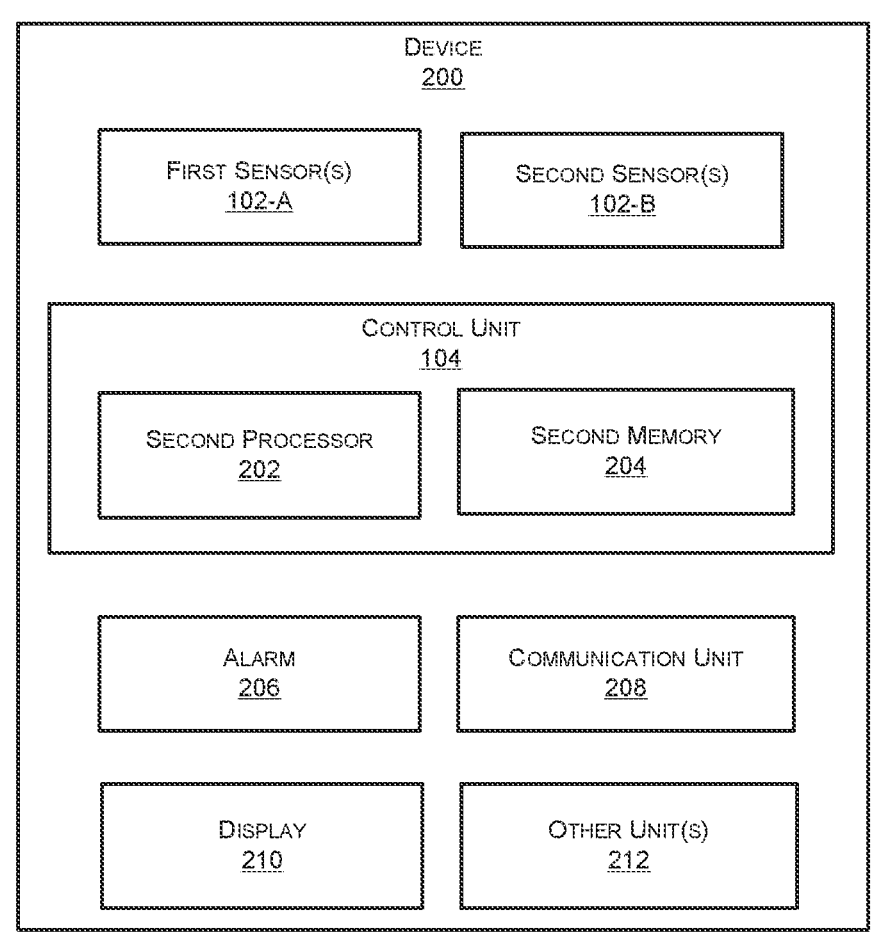
*FIG. 2*

500

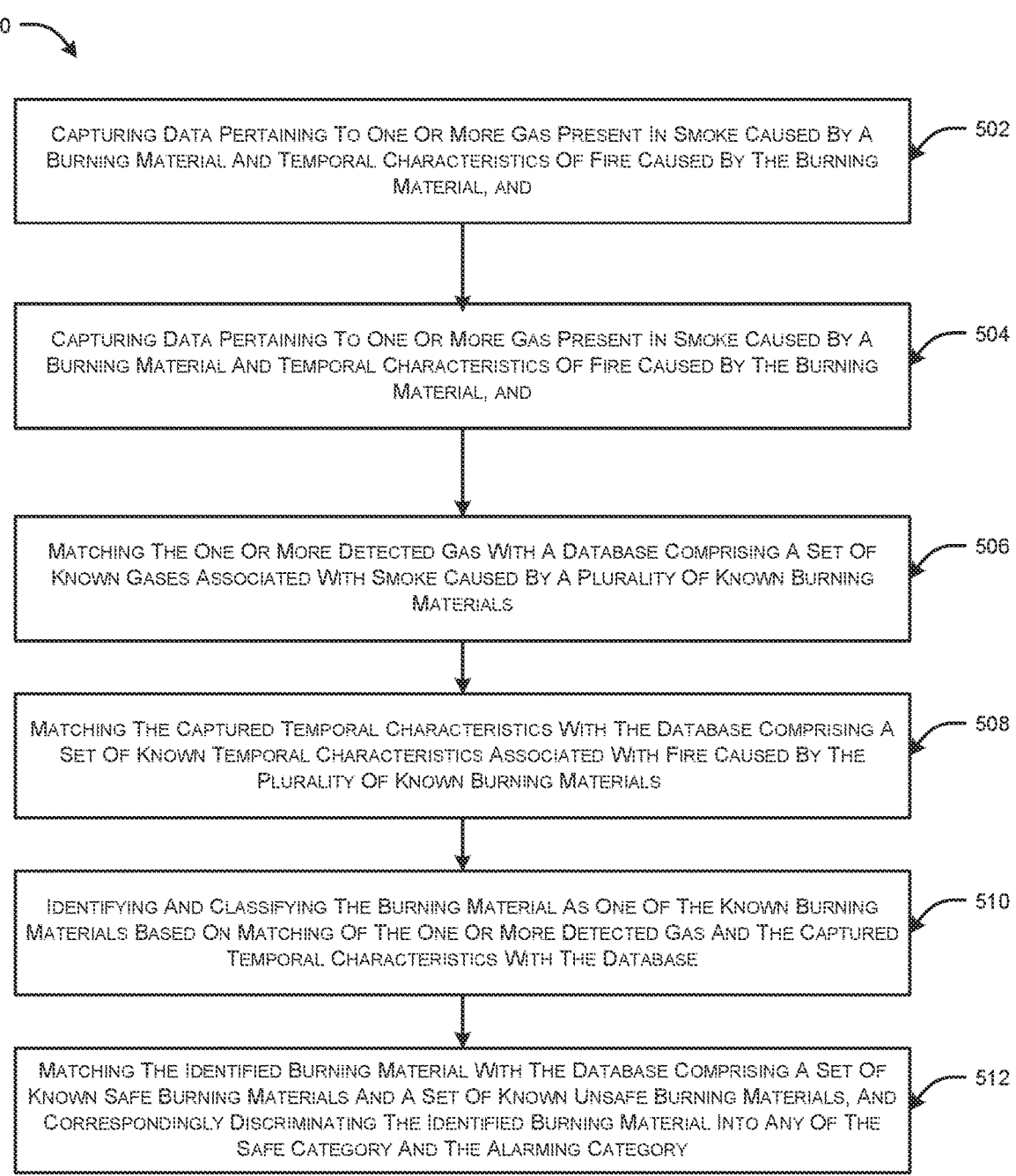

CAPTURING DATA PERTAINING TO ONE OR MORE GAS PRESENT IN SMOKE CAUSED BY A BURNING MATERIAL AND TEMPORAL CHARACTERISTICS OF FIRE CAUSED BY THE BURNING MATERIAL, AND                                        502

CAPTURING DATA PERTAINING TO ONE OR MORE GAS PRESENT IN SMOKE CAUSED BY A BURNING MATERIAL AND TEMPORAL CHARACTERISTICS OF FIRE CAUSED BY THE BURNING MATERIAL, AND                                        504

MATCHING THE ONE OR MORE DETECTED GAS WITH A DATABASE COMPRISING A SET OF KNOWN GASES ASSOCIATED WITH SMOKE CAUSED BY A PLURALITY OF KNOWN BURNING MATERIALS                                        506

MATCHING THE CAPTURED TEMPORAL CHARACTERISTICS WITH THE DATABASE COMPRISING A SET OF KNOWN TEMPORAL CHARACTERISTICS ASSOCIATED WITH FIRE CAUSED BY THE PLURALITY OF KNOWN BURNING MATERIALS                                        508

IDENTIFYING AND CLASSIFYING THE BURNING MATERIAL AS ONE OF THE KNOWN BURNING MATERIALS BASED ON MATCHING OF THE ONE OR MORE DETECTED GAS AND THE CAPTURED TEMPORAL CHARACTERISTICS WITH THE DATABASE                                        510

MATCHING THE IDENTIFIED BURNING MATERIAL WITH THE DATABASE COMPRISING A SET OF KNOWN SAFE BURNING MATERIALS AND A SET OF KNOWN UNSAFE BURNING MATERIALS, AND CORRESPONDINGLY DISCRIMINATING THE IDENTIFIED BURNING MATERIAL INTO ANY OF THE SAFE CATEGORY AND THE ALARMING CATEGORY                                        512

*FIG. 5*

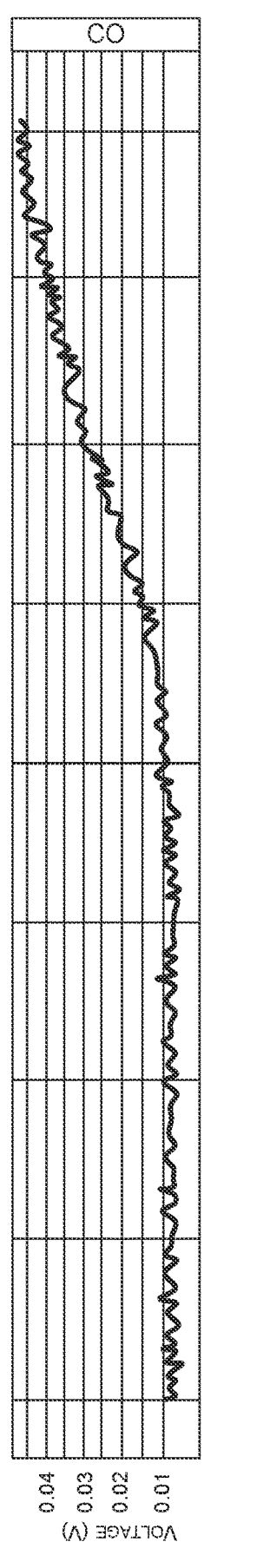
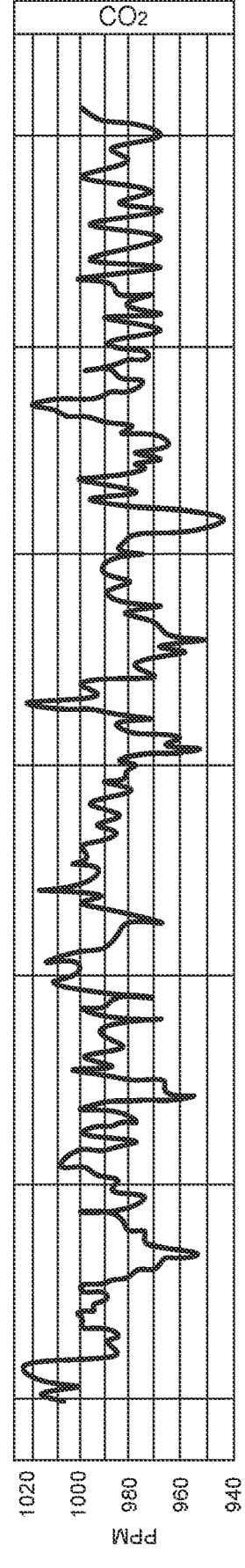
*FIG. 6B*

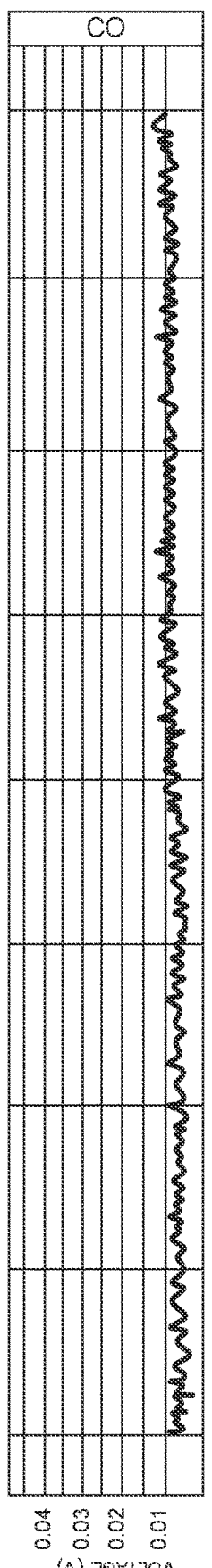
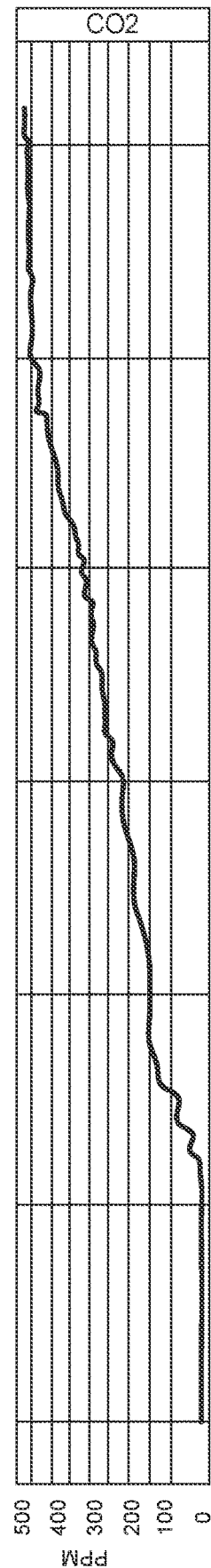
FIG. 7B

SYSTEM, DEVICE, AND METHOD FOR SMOKE DISCRIMINATION AND IDENTIFICATION OF FIRE SOURCE

CROSS-REFERENCE TO RELATED APPLICATION

This patent application claims the benefit of priority of European Provisional Patent Application No. EP22382964.9, filed on Oct. 11, 2022.

TECHNICAL FIELD

This invention relates to the field of fire and smoke detection, and more particularly, to a system, device, and method for smoke/fire discrimination and identification of the fire and/or pollution-causing source.

BACKGROUND

In existing fire detection systems, smoke may also be caused by some nuisance or non-alarming sources, which may be mistakenly considered to be a real fire, leading to the generation of a false alarm. In addition, the existing systems are incapable of discriminating between a real (alarming) fire and a non-alarming fire, which may lead to false alarm generation. Besides, the existing systems may also be incapable of identifying the fire or smoke-causing material. There is, therefore, a need to provide a solution that can discriminate between a real (alarming) fire and a non-alarming fire, and can further identify the fire or smoke-causing material.

SUMMARY

Described herein is a system for smoke discrimination and identification of fire source is provided. The system comprises a control unit comprising a processor operatively coupled to a memory storing instructions executable by the processor, The control unit is configured to receive data pertaining to one or more gas present in the smoke generated by a burning material, receive data pertaining to temporal characteristics of fire caused by the burning material, identify the burning material based on the data pertaining to the one or more gas and the data pertaining to temporal characteristics of fire; and trigger a fire event based on the identified burning material.

In one or more embodiment, the control unit is configured to identify the burning material using a temporal model of a machine learning system, the temporal model configured to determine the burning material based on the temporal characteristics of fire.

In one or more embodiments, the control unit is configured to match the one or more detected gas with a database comprising a set of known gases associated with smoke generated by a plurality of known burning materials, match the captured temporal characteristics with the database comprising a set of known temporal characteristics associated with fire caused by the plurality of known burning materials, identify and classify the burning material as one of the known burning materials based on matching of the one or more detected gas and the captured temporal characteristics with the database, match the identified burning material with the database comprising a set of known safe burning materials and a set of known unsafe burning materials, and correspondingly discriminate the identified burning material into any of the safe category and the alarming category.

In one or more embodiments, the control unit is configured to discriminate the identified unsafe burning material into any of an organic fire source material, a liquid fire source material, and a synthetic fire source material.

In one or more embodiments, the system comprises one or more first sensor in communication with the control unit and configured to detect the one or more gas present in the smoke generated by the burning material, and one or more second sensor in communication with the control unit and configured to capture the temporal characteristics of fire caused by the burning material.

In one or more embodiments, the system comprises a multi-type wave sensor in communication with the control unit and configured to capture multi-dimensional and temporal characteristics of the fire and smoke caused by the burning material.

In one or more embodiments, the control unit is configured to match the captured multi-dimensional and temporal characteristics of the fire and smoke with the database comprising a set of known multi-dimensional and temporal characteristics associated with smoke and fire caused by the plurality of known burning materials, and correspondingly identify and classify the burning material as one of the known burning materials.

In one or more embodiments, the one or more first sensor comprises one or more gas sensors, and wherein the one or more second sensor comprises one or more of a photodiode, and temperature sensor.

Also described herein is a device for smoke discrimination and identification of fire source is provided. The device comprises one or more first sensor operable to detect one or more gas present in smoke generated by a burning material, one or more second sensor operable to capture temporal characteristics of fire caused by the burning material, and a control unit operatively coupled to the one or more first sensor and the one or more second sensors. The control unit is configured to receive data pertaining to the one or more detected gas and receive data pertaining to the captured temporal characteristics. The control unit is configured to identify the burning material based on the data pertaining to the one or more gas and the data pertaining to temporal characteristics of fire, and trigger a fire event based on the identified burning material.

In one or more embodiments, the device is adapted to be configured within an aspirating fire detection device that is configured to receive the smoke present in an area of interest (AOI) and facilitate the flow of the received smoke through the device to allow the identification and discrimination of the smoke and the corresponding burning material.

In one or more embodiments, the device is adapted to be installed at predefined positions at an AOI and configured to identify and discriminate the smoke and the corresponding burning material present at the AOI.

Further described herein is a method for smoke discrimination and identification of fire source is provided. The method comprises the steps of capturing data pertaining to one or more gas present in smoke caused by a burning material and temporal characteristics of fire caused by the burning material, identifying the burning material based on the data pertaining to the one or more gas and the data pertaining to temporal characteristics of fire, and triggering a fire event based on the identified burning material.

In one or more embodiments, the method comprises the step of matching the one or more detected gas with a database comprising a set of known gases associated with smoke caused by a plurality of known burning materials, matching the captured temporal characteristics with the database comprising a set of known temporal characteristics associated with fire caused by the plurality of known burning materials, and identifying and classifying the burning material as one of the known burning materials based on matching of the one or more detected gas and the captured temporal characteristics with the database, matching the identified burning material with the database comprising a set of known safe burning materials and a set of known unsafe burning materials, and correspondingly discriminating the identified burning material into any of the safe category and the alarming category.

In one or more embodiments, the method comprises the step of generating an alarm signal when the burning material is identified to be in the alarming category.

In one or more embodiments, the method comprises the step of generating an alarm signal when a concentration of the one or more detected gas exceeds a first threshold value, and/or a level of the captured temporal characteristics exceeds a second threshold value.

In one or more embodiments, the method comprises the step of discriminating the identified unsafe burning material into any of an organic fire source material, a liquid fire source material, and a synthetic fire source material.

In one or more embodiments, the method comprises the steps of capturing multi-dimensional and temporal characteristics of the fire and smoke caused by the burning material, and comparing the captured multi-dimensional and temporal characteristics with the database comprising a set of known multi-dimensional and temporal characteristics associated with fire caused by the plurality of known burning materials, and correspondingly identifying and classifying the burning material as one of the known burning materials.

The foregoing summary is illustrative only and is not intended to be in any way limiting. In addition to the illustrative aspects, embodiments, and features described above, further aspects, embodiments, features, and techniques of the invention will become more apparent from the following description taken in conjunction with the drawings.

BRIEF DESCRIPTION OF THE DRAWINGS

The accompanying drawings are included to provide a further understanding of the subject disclosure of this invention and are incorporated in and constitute a part of this specification. The drawings illustrate exemplary embodiments of the subject disclosure and, together with the description, serve to explain the principles of the subject disclosure.

In the drawings, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

FIG. 1 is a block diagram illustrating an exemplary architecture of a system for smoke/fire discrimination and identification of the fire source (burning material) in accordance with one or more embodiments of the invention.

FIG. 2 is a block diagram illustrating the functional modules of a device for smoke/fire discrimination and identification of the burning material in accordance with one or more embodiments of the invention.

FIG. 5 is a flow chart illustrating an exemplary embodiment of a method for smoke/fire discrimination and identification of the burning material in accordance with one or more embodiments of the invention.

FIG. 6B illustrates an exemplary graph depicting the concentration of gases detected in the smoke caused by the wood fire in accordance with one or more embodiments of the invention.

FIG. 7B illustrates an exemplary graph depicting the concentration of gases detected in the smoke generated during nuisance cooking in accordance with one or more embodiments of the invention.

DETAILED DESCRIPTION

Figure 3:
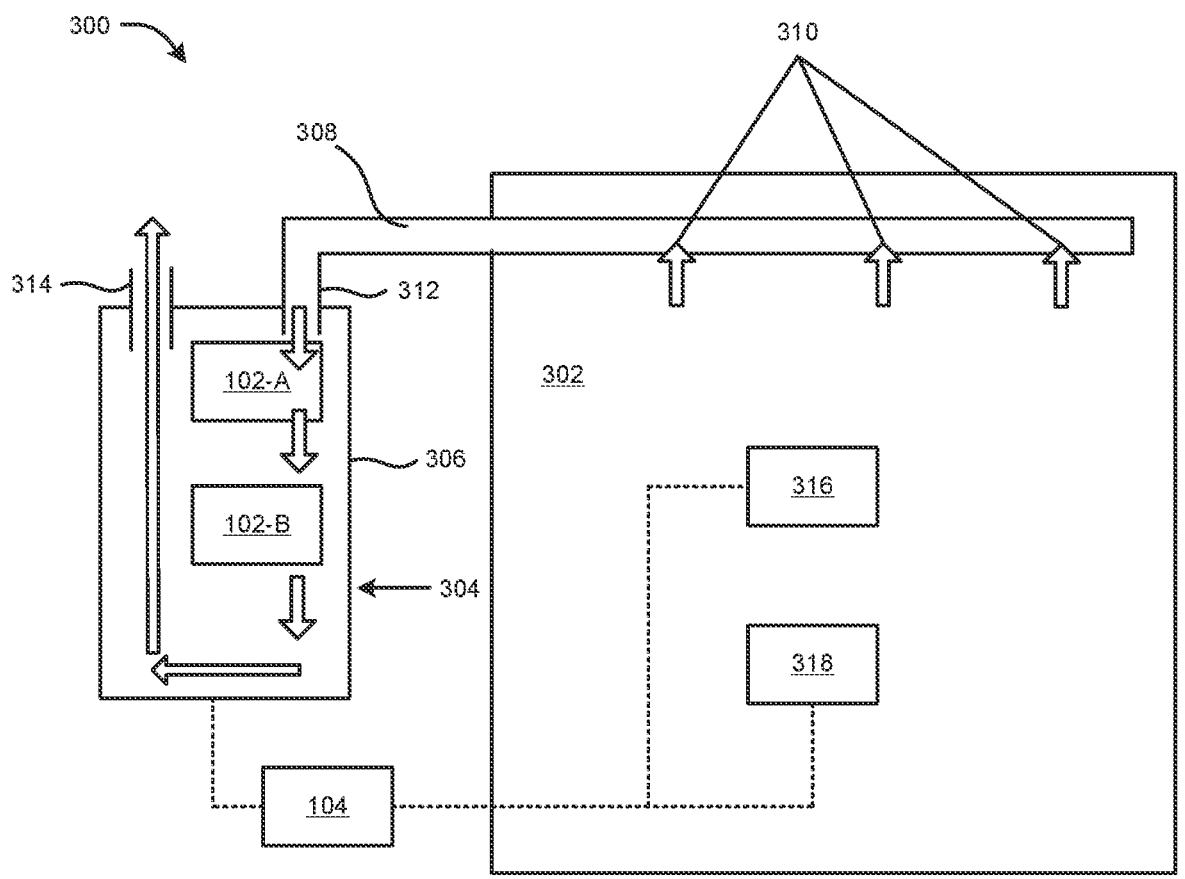
FIG. 3 is a schematic diagram illustrating the device/system being configured within an aspirating fire detection device in accordance with one or more embodiments of the invention.

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the subject disclosure as defined by the appended claims.

Various terms are used herein. To the extent a term used in a claim is not defined below, it should be given the broadest definition persons in the pertinent art have given that term as reflected in printed publications and issued patents at the time of filing.

Every material upon burning generates smoke and/or fire that has a unique gas emission and a unique temporal characteristic that is reflected in the gas present in the smoke and temporal characteristic of the fire. The invention (system, device, and method) captures the unique gas emission and the unique temporal characteristic of the fire caused by the burning material using the first sensors, and the second sensors. The control unit then matches the data captured by the first sensors and the second sensors with the database storing the details of already known burning materials, to identify the burning material and further discriminate the burning material or the smoke/fire caused into a non-alarming (safe) category or an alarming category. In addition, the control unit can identify and classify the burning material as one of the known burning materials based on a voting consensus between one or more nodes comprising gas sensors, temporal characteristic sensors, smoke sensors, multi-type wave sensors, and a machine learning engine associated with the control unit.

Referring to FIG. 1, the system 100 for smoke/fire discrimination and identification of the smoke/fire source (burning material/polluting material) causing the smoke/fire or air pollution is provided. The system 100 includes a gas detector that comprises one or more gas sensors 102-A (also referred to as first sensors 102-A, herein), and a temporal characteristic monitoring device that comprises one or more temporal characteristic capturing sensors 102-B (also referred to as second sensors 102-B, herein). The system 100 further includes a control unit 104 (or controller) that is operatively coupled to the first sensors 102-A and the second sensors 102-B. In one or more embodiments, the first sensors 102-A and the second sensors 102-B are installed at desired positions at a location or area of interest (AOI) or environment. Further, the sensors 102-A, 102-B remain in communication with the control unit 104 via wireless media, through a network. In other embodiments, the first sensors 102-A and the second sensors 102-B are operatively connected to the control unit 104 via wired media.

Referring to FIG. 2, the device 200 for smoke/fire discrimination and identification of the smoke/fire source (burning material) or pollution-causing material is provided. The device 200 includes the first sensors 102-A, the second sensors 102-B, and the control unit 104 of the system of FIG. 1 being accommodated in a single housing, forming a stand-alone device that is easily installable at a desired location or an area of interest (AOI). The device 200 is adapted to receive the smoke across the first sensors 102-A for sensing the gases present in the smoke or pollution (environmental or industrial), and also allows the second sensors 102-B to capture the temporal characteristics of the fire caused by the burning material. The detailed operation of the device 200 has been described later in conjunction with FIG. 2.

The gas sensors or first sensors 102-A of the invention are operable to detect and monitor the concentration of one or more gas present in the smoke generated by a burning material (fire source) or the gases present in the pollution caused by the polluting material. The gases present in the smoke or pollution can be carbon dioxide ($CO_2$), carbon monoxide (CO), and methane ($CH_4$), but not limited to the like. Further, the temporal characteristics sensor or second sensor 102-B can include one or more of a photodiode, temperature sensor, and the like. The second sensors 102-B are operable to capture temporal characteristics of fire caused by any burning material. The gas signature detection process and the temporal matching process may generally work in parallel. In addition, in one or more embodiments, the gas signature detection process and the temporal matching process may also work sequentially.

In one or more embodiments, the gas sensor 102-A used in the system 100 and device 200 can be an infrared gas sensor that generally operates on the principle that when infrared radiation interacts with gas molecules, infrared light is absorbed by the gas molecules at a particular wavelength, causing vibration of the gas molecules. These gas sensors detect a decrease in transmitted infrared light which is in proportion to the gas concentration. This transmittance, the ratio of transmitted radiation energy to the incident energy, is dependent on the target gas concentration. The infrared gas sensor consists of an infrared source, detector, optical filter, gas cell, and electronics for signal processing. The infrared light that is absorbed by a target gas passes through the active filter with a particular bandwidth for the detection of the target gas. The infrared light that does not interact with the target gas passes through the reference filter. The difference between transmitted light intensities in these two bandwidths is converted into gas concentration. However, in other embodiments, other types of gas sensors including chemical gas sensors, semiconductor-based gas sensors, and the like can also be used for detecting the gases present in the smoke/pollution.

In one or more embodiments, the invention includes a multi-type wave sensor that is configured to capture multi-dimensional and temporal characteristics of the fire and smoke caused by unknown burning/polluting material. The use of a multi-type wave sensor allows the detection of light waves of different wavelengths while detecting the concentration of gases in the smoke or pollution. Thus, the individual performance of the sensors is improved and the overall smoke/fire discrimination capability of the invention is also improved.

Each material upon burning generates smoke and/or fire that has a unique gas emission and a unique temporal characteristic that is reflected in the gas present in the smoke and temporal characteristic of the fire. Similarly, a specific set of gases is also reflected in environmental or industrial pollution. The invention captures the unique gas emission and the unique temporal characteristic of the smoke/fire caused by the burning/polluting material using the first sensors 102-A, and the second sensors 102-B. The control unit 104 then processes the data captured by the first sensors 102-A and the second sensors 102-B to identify burning/polluting material and further discriminate the material or the smoke/fire caused into a non-alarming (safe) category or an alarming category.

The control unit 104 matches the gas detected by the first sensors 102-A with a database comprising a set of known gases associated with smoke or pollution caused by a plurality of known burning/polluting materials. Further, the control unit 104 matches the captured temporal characteristics with a database 124 comprising a set of known temporal characteristics associated with smoke/fire caused by the plurality of known burning materials. Accordingly, the control unit 104 identifies and further classifies the burning material as one of the known materials based on matching of the detected gas and the captured temporal characteristics with the database of known materials. In addition, the control unit 104 identifies and further classifies the pollution-causing material as one of the known materials based on matching of the detected gas and the captured temporal characteristics with the database of known materials. Further, the control unit 104 discriminates the identified burning material into an organic fire source material, a liquid fire source material, and a synthetic fire source material based on matching of the identified burning material with the database 124 of known materials.

The database 124 is pre-stored with the list of known burning (combustible) materials or fire sources and pollution-causing materials, including the alarming and non-alarming categories, along with the corresponding gas data and temporal characteristic data of smoke/fire caused by all these known burning/polluting materials. In one or more embodiments, the database 124 can be associated with the control unit 104 and reside in the same device for offline operation. In other embodiments, the database 124 can be associated with a central server that remains in communication with the control unit 104 of the system 100 or device 200.

In one or more embodiments, if the smoke/fire caused by the burning/polluting material is found to be in the alarming category, the control unit 104 considers the detected fire/smoke as a real fire or an alarming pollution level and correspondingly triggers an alarm system. For instance, if the cause of the fire/smoke is identified to be a burning material such as wood, fuel, plastic, synthetic material, and the like, the control unit 104 considers the fire/smoke as a real fire and correspondingly triggers the alarm system. Further, if the smoke/fire caused by the burning material is found to be in the non-alarming category, the control unit 104 does not trigger the alarm system, thereby eliminating the chances of any false alarm triggering. For instance, if the cause of the fire/smoke is identified to be created by some nuisance or non-alarming sources like barbeque, cooking smoke or steam generated while cooking, and the like, the control unit 104 considers the fire/smoke as a nuisance or non-alarming fire. In addition, if the pollution level or severity is found to be unsafe and alarming, the control unit 104 correspondingly triggers the alarm system.

Figure 6A:
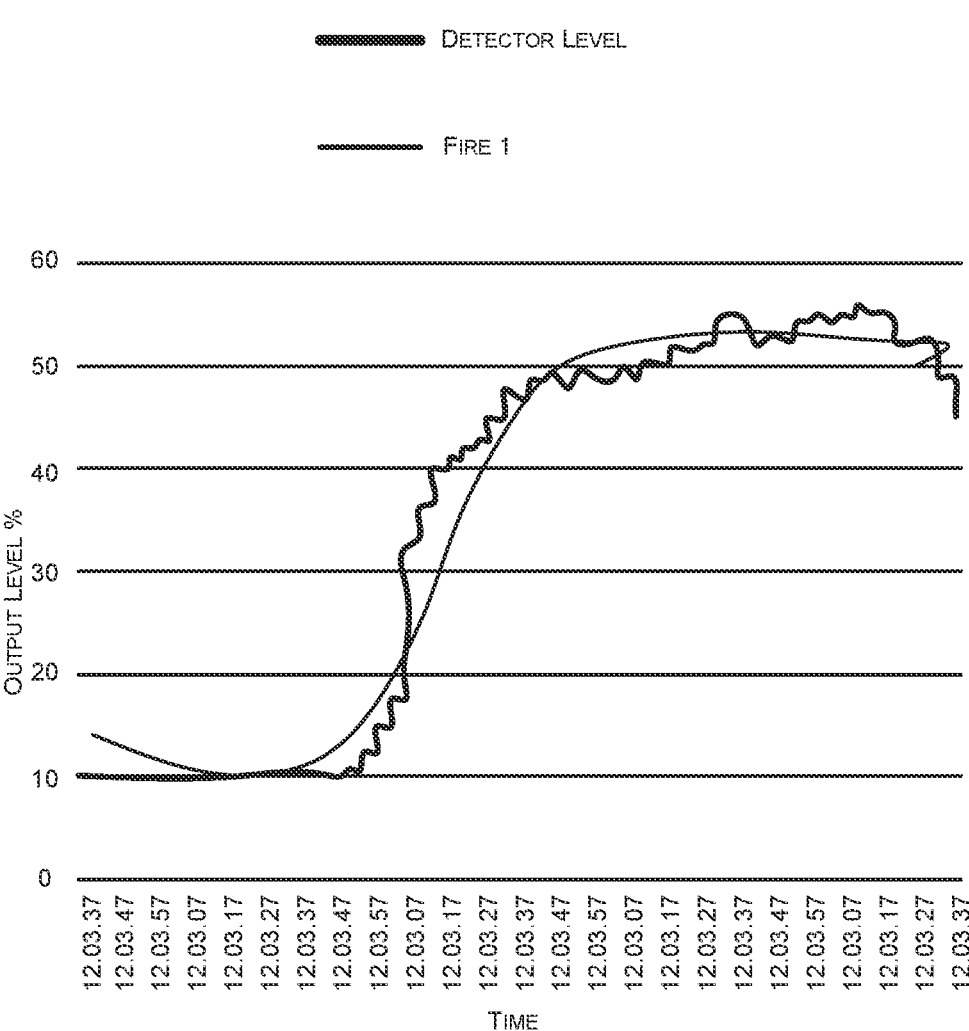
FIG. 6A illustrates an exemplary temporal characteristic of a wood fire in accordance with one or more embodiments of the invention.

In one example, referring to FIGS. 6A and 6B, if $CO_2$ and CO gases are detected in the smoke caused by an unknown burning material and the concentration of the detected $CO_2$ and CO gases matches that of smoke caused by burning wood as shown in FIG. 6A, and further if the temporal characteristic of fire caused by the unknown burning material also matches with the known temporal characteristics of fire caused by burning wood as shown in FIG. 6B, the control unit 104 identifies the unknown burning material i.e., the source of smoke/fire as wood. Furthermore, as the identified burning material i.e., wood falls in the database of alarming category, the control unit 104 triggers the alarm.

Figure 7A:
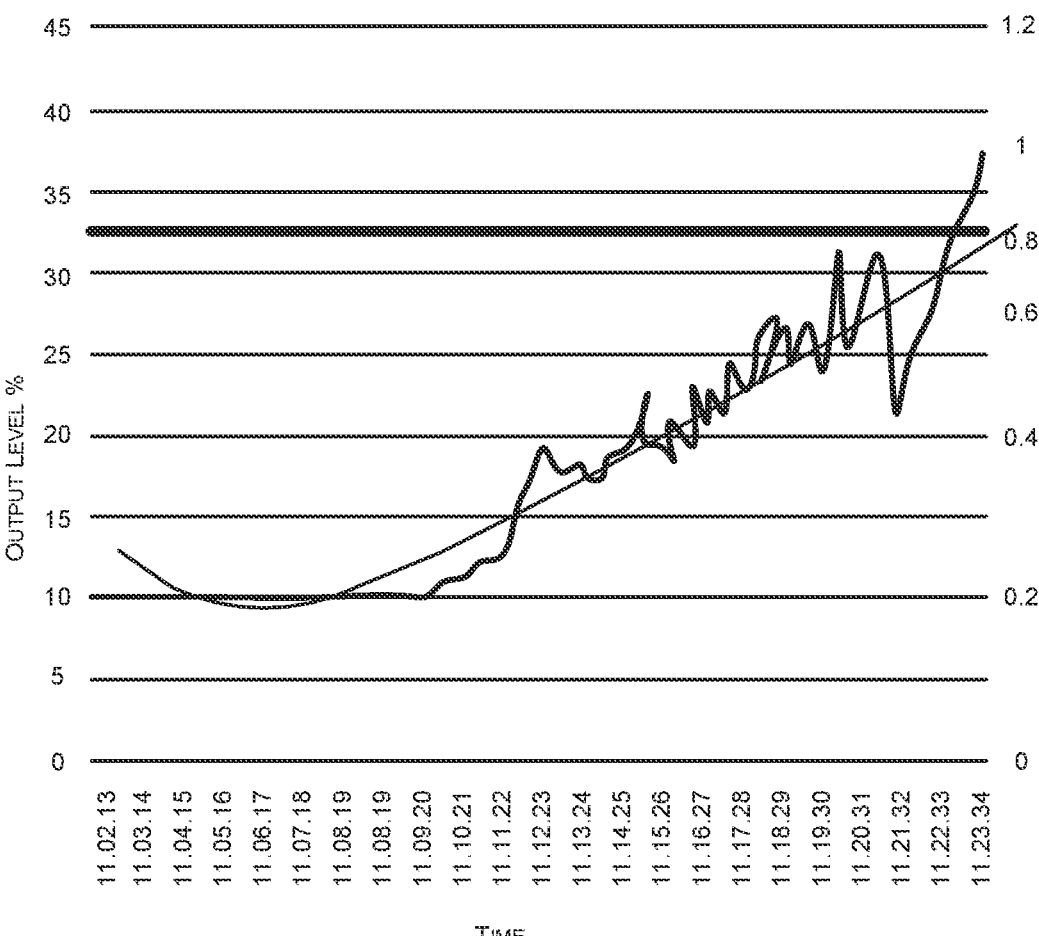
FIG. 7A illustrates an exemplary temporal characteristic of fire generated during nuisance cooking in accordance with one or more embodiments of the invention.

In another example, referring to FIGS. 7A and 7B, if $CO_2$ and CO gases are detected in the smoke caused by an unknown burning material and the concentration of the detected $CO_2$ and CO gases matches that of smoke generated while cooking as shown in FIG. 7A, and further if the temporal characteristic of fire caused by the unknown burning material also matches with the known temporal characteristics of fire caused during cooking as shown in FIG. 7B, the control unit 104 identifies the unknown burning material i.e., the source of smoke/fire as a cooking source. Furthermore, as the identified burning material i.e., wood falls in the database of the non-alarming (safe) category, the alarm system is not triggered by the control unit 104, thereby preventing false alarm generation.

In one or more embodiments, the system 100 and device 200 include the multi-type wave sensor that remains in communication with the control unit 104. The sensors are configured to capture multi-dimensional and temporal characteristics of the fire and smoke caused by unknown burning material or gases present in pollution. In such embodiments, the control unit 104 matches the captured multi-dimensional and temporal characteristics of the fire and smoke caused by the unknown burning material or pollution-causing material with the database 124 comprising a set of known multi-dimensional and temporal characteristics associated with smoke and fire caused by the plurality of known burning materials. Accordingly, the control unit 104 identifies and further classifies the unknown burning/polluting material as one of the known burning/polluting materials. Further, the control unit 104 also determines if the identified burning/polluting material falls within an alarming category or a non-alarming category as already explained above in detail.

Figure 4:
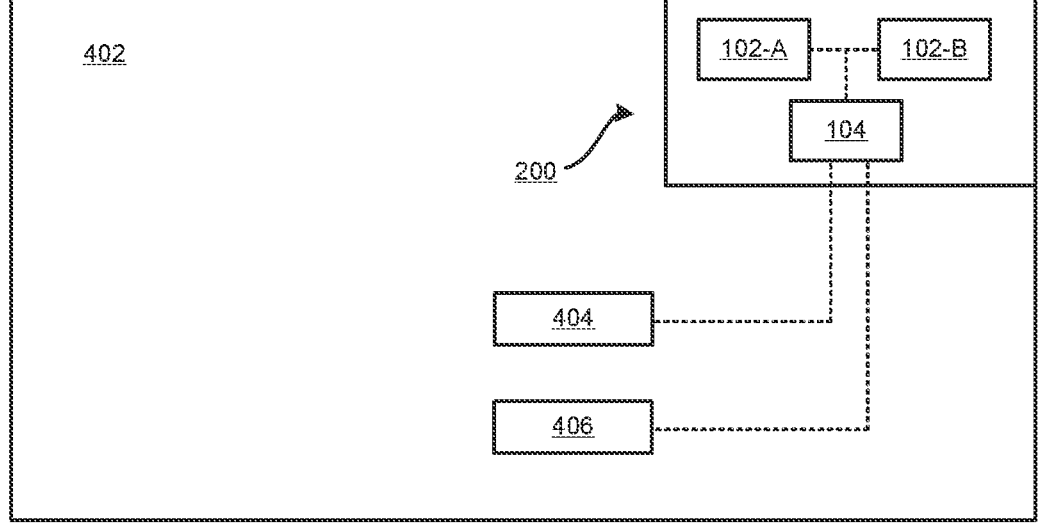
FIG. 4 is a schematic diagram illustrating the device/system being configured within an area of interest such as a room in accordance with one or more embodiments of the invention.

In one or more embodiments, the system 100 or device 200 is implemented in an aspirating fire detection device 300 as shown in FIG. 3, where the aspirating device 300 receives the smoke present at the AOI or receives pollution from outside and facilitates the flow of the received smoke or pollution through the device 200 to enable identification and discrimination of the smoke and the corresponding burning material by the device 200. The detailed operation of the device 200 has been described later in conjunction with FIG. 3. In other embodiments, the device 200 or the components of the system 300 are directly installed at a predefined position in the AOI as shown in FIG. 4, where the device 200 or system 100 identifies and discriminates the smoke and the corresponding burning material present at the AOI.

Referring back to FIG. 1, the functional modules of the system 100 and control unit 104 are disclosed. Although the invention has been explained considering that system 100 is implemented by the control unit 104, it may be understood that system 100 may also be implemented in a variety of computing systems, such as a laptop computer, a desktop computer, a notebook, a workstation, a server, a network server, a cloud-based environment and the like. The control unit 104 comprises one or more processor(s) 106 (first processor) operatively coupled to a memory 108 (first memory). The processor 106 may be implemented as one or more microprocessors, microcomputers, microcontrollers, digital signal processors, central processing units, logic circuitries, and/or any devices that manipulate data based on operational instructions. Among other capabilities, processor 106 is configured to fetch and execute computer-readable instructions stored in the memory 108. The memory 108 may store one or more computer-readable instructions or routines, which may be fetched and executed to create or share the data units over a network service. The memory 108 may comprise any non-transitory storage device including, for example, volatile memory such as RAM, or non-volatile memory such as EPROM, flash memory, and the like.

The control unit 104 also comprises an interface(s) 110 that may comprise a variety of interfaces, for example, interfaces for data input and output devices, referred to as I/O devices, storage devices, and the like. The control unit 104 further includes a communication unit 112 such as WiFi module, transceiver, Bluetooth module, cellular connection module such as 2G, 3G, 4G, and 5G, and the like to facilitate communication of the control unit 104 with the sensors 102-A, 102-B, a fire system or alarm system, and mobile devices associated with users of the invention, through the network. The interface(s) 110 may also provide a communication pathway for one or more internal components or units of the control unit 104. Examples of such internal components include, but are not limited to, processing engine(s) 114 and database 124.

The processing engine(s) 114 is implemented as a combination of hardware and programming (for example, programmable instructions) to implement one or more functionalities of the processing engine(s) 114. In the examples described herein, such combinations of hardware and programming may be implemented in several different ways. For example, the programming for the processing engine(s) 114 may be processor-executable instructions stored on a non-transitory machine-readable storage medium and the hardware for the processing engine(s) 114 may comprise a processing resource (for example, one or more processors), to execute such instructions. In the present examples, the machine-readable storage medium may store instructions that, when executed by the processing resource, implement the processing engine(s). In such examples, the control unit 104 comprises the machine-readable storage medium storing the instructions and the processing resource to execute the instructions, or the machine-readable storage medium may be separate but accessible to server 102 and the processing resource. In other examples, the processing engine(s) may be implemented by an electronic circuitry. The database may comprise data that is either stored or generated as a result of functionalities implemented by any of the components of the processing engine(s) 114 or system 100.

In one or more embodiments, the processing engine(s) 114 includes a gas detection unit 116, a temporal characteristic unit 118, a Hidden Markov Models (HMM) unit or Redundant Neural Networks (RNN) unit 120, an alarm unit 122, and other units (s). Other unit(s) can supplement the functionalities of the processing engine or the control unit 104. The database 124 is pre-stored with the list of known burning (combustible) materials or fire sources, along with the corresponding gas data and temporal characteristic data of fire caused by all these known burning materials.

In one or more embodiments, the gas detection unit 116 enables the control unit 104 to allow the first sensors 102-A to detect gas present in the smoke caused by an unknown burning material and receive the detected gas data from the first sensors 102-A. The gas detection unit 116 also enables the control unit 104 to allow the first sensors 102-A to detect gas present in pollution at an AOI or outside and receive the detected gas data from the first sensors 102-A. The gas detection unit 116 further enables the control unit 104 to match the concentration of gases detected in the smoke or pollution with the database 124 comprising the concentration of known gases associated with smoke generated by the plurality of known burning materials or by the pollution-causing materials.

In one or more embodiments, the temporal characteristic unit 118 enables the control unit 104 to allow the second sensors 102-B to capture the temporal characteristic of fire caused by the unknown burning material and receive the captured temporal characteristic data from the second sensors 102-B. The temporal characteristic unit 118 further enables the control unit 104 to match the temporal characteristic of the fire caused by the unknown burning material with the database 124 comprising the temporal characteristic of fire caused by the plurality of known burning materials.

In one or more embodiments, temporal characteristic unit 118 may include a machine learning system configured to identify the burning material based on the temporal characteristics using one or more temporal models. For example, in one or more embodiments, the HMM/RNN unit 120 may be configured to enable the temporal characteristic unit to detect and classify the temporal characteristic of fire by using any of the temporal pattern recognition technologies, such as Hidden Markov Models (HMM) or Redundant Neural Networks (RNN), however, other temporal pattern recognition technologies may also be employed. For example, the machine learning models may include decision trees, support vector machines, regression analysis, Bayesian networks, random forest learning, dimensionality reduction algorithms, boosting algorithms, artificial neural networks (e.g., fully connected neural networks, deep convolutional neural networks, or recurrent neural networks) and/or other machine learning models. In one or more embodiments, the machine learning system may be configured to train the one or mode temporal models to identify the burning material. In one or more embodiments, the machine learning system may use one or more of supervised learning, semi-supervised, unsupervised learning, reinforcement learning, and/or other machine learning techniques.

Accordingly, the gas detection unit 116 and the temporal characteristic unit 118 enable the control unit 104 to identify and classify the unknown material as one of the known burning materials based on matching of the gas detected by the first sensors 102-A and the temporal characteristics captured by the second sensors 102-B, with the database 124 of known materials. In addition, the gas detection unit 116 and the temporal characteristic unit 118 enable the control unit 104 to match the identified burning material with the database 124 comprising the set of known safe burning materials and set of known unsafe burning materials, which enables the control unit 104 to discriminate the identified burning material into any of the safe category and the alarming category. Further, the gas detection unit 116 and the temporal characteristic unit 118 enable the control unit 104 to match the identified pollution causing material with the database 124 comprising the set of known safe polluting materials and set of known unsafe polluting materials, which enables the control unit 104 to discriminate the identified polluting material into any of the safe category and the alarming category. Furthermore, the gas detection unit 116 and the temporal characteristic unit 118 enable the control unit 104 to discriminate the identified unsafe burning/polluting material into an organic source material, a liquid source material, and a synthetic fire source material.

In one or more embodiments, when multi-type wave sensors are used in the system or device, the control unit 104 enables the multi-type wave sensors to capture multi-dimensional and temporal characteristics of the fire and smoke caused by the unknown burning/polluting material. Further, the gas detection unit 116 and the temporal characteristic unit 118 enable the control unit 104 to match the captured multi-dimensional and temporal characteristics of the fire and smoke with the database 124 comprising a set of known multi-dimensional and temporal characteristics associated with smoke and fire caused by the plurality of known burning/polluting materials, and correspondingly identify and classify the burning/polluting material as one of the known burning/polluting materials.

In one or more embodiments, the process of decision-making by the control unit 104 to identify and discriminate fire/smoke causing material, can be based on the decision-making theory of distributed systems, in particular voting algorithms. In such voting algorithms, a consensus is determined by the interaction of the different nodes of the system 100. For instance, a node may be the first sensor 102-A, the second sensor 102-B, the temporal ML engine (HMMRNN unit), a traditional smoke sensor or a gas sensor, and the like.

Each node, based on the result of its own processing and the result of other (some or all) nodes, emits a vote about the question to be answered. For example, the question can be "has a specific type of substance (say X) detected in the air?" or "is there a burning fire that needs to be signaled?" or even "the probability of detecting the specific material X is Y" or "the sensor that has a bigger probability of being active is Z", and the likes. The votes of all nodes are transmitted to the control unit 104. Further, using one of a variety of voting algorithms (exact/inexact/approval/and the likes) a consensus is met, and accordingly, a decision is made. This kind of decision-making may be safer and may help minimize the number of false positives and false negatives.

Further, in order to minimize the number of false negatives, which is a safety requirement, a (negative) veto may be employed in the algorithm in one or more embodiments. For example, the system 100 may at least incorporate the sensor 102, so that it can be used as a baseline for safety. For instance, even if the voting algorithm consensus suggests that there is no fire and the sensor 102 decides that there is a fire, a fire event (e.g., a fire alarm) is triggered by the control unit 104. This may help lower the number of false negatives, thereby meeting another safety requirement.

Accordingly, the control unit 104 can identify and classify the burning material as one of the known burning materials based on a voting consensus between one or more nodes including the smoke sensors or gas sensor, and the HMM/RNN unit associated with the control unit 104.

In one or more embodiments, the alarm unit 122 enables the control unit 104 to actuate the alarm system of the device or a fire alarm system associated with the AOI when the burning/polluting material is identified to be in the alarming category. Further, the alarm unit 122 also enables the control unit 104 to actuate the alarm system of the device or the fire alarm system when the concentration of the detected gas in the smoke caused by the burning/polluting material exceeds a first threshold value, and/or a level of the temporal characteristics of the fire caused by the burning/polluting material exceeds a second threshold value.

Referring back to FIG. 2, an exemplary block diagram of the device 200 is provided. The device 200 includes a processor 202 (second processor), a memory 204 (second memory), the first sensors 102-A, the second sensors 102-B, an alarm 206, and a communication unit (such as a transceiver) 208, being configured within a single housing that can be easily positioned at a predefined location. The processor 202 is coupled to the memory 204, the sensors 102-A, 102-B, the transceiver 208, and the alarm 206. The processor 202 and memory 204 collectively form the control unit 104, where the processor 202 includes suitable logic, circuitry, and/or interfaces that are operable to execute one or more instructions stored in the memory to perform a predetermined operation. The memory 204 may be operable to store one or more instructions. The processor 202 may be implemented using the processors known in the art. Some of the commonly known memory implementations include, but are not limited to, a random access memory (RAM), a read only memory (ROM), a hard disk drive (HDD), and a secure digital (SD) card. Further, the memory includes the one or more instructions that are executable by the processor to perform specific operations. It is apparent to a person having ordinary skills in the art that the one or more instructions stored in the memory enable the hardware of the device to perform the predetermined operations.

In some embodiments, the first sensors 102-A of the device 200 are operable to detect one or more gas present in the smoke generated by burning/polluting material. The first sensors 102-A include gas sensors including but are not limited to a $CO_2$ sensor, CO sensor, and the likes, which are already known in the art. The second sensors 102-B of the device 200 are operable to capture temporal characteristics of fire caused by the burning material. The second sensors 102-B include but are not limited to temperature sensors, light sensors, and the like, which are already known in the art. The data captured by the sensors 102-A, 102-B are then transmitted to the processor or control unit 104 for further processing as already explained in detail in FIG. 1.

In one or more embodiments, the sensors are multi-type wave sensors that are operable to capture multi-dimensional and temporal characteristics of the fire and smoke caused by the burning/polluting material. Those skilled in the art would appreciate that the use of a multi-type wave sensor allows the detection of reflected light waves of different wavelengths while detecting the gases and gas concentration in the smoke/pollution. As a result, the individual performance of the sensors is improved and the overall smoke/fire discrimination capability of the invention is also improved.

The communication unit 208 (transceiver) transmits captured data to the mobile devices of the users or to the fire detection and alarm system. Examples of the transceiver 208 may include but are not limited to, an antenna, an Ethernet port, an USB port, or any other port that can be configured to transmit the captured data.

The transceiver 208 transmits data in accordance with the various communication protocols, such as TCP/IP, UDP, and 2G, 3G, or 4G communication protocols. The alarm 206 of the device 200 includes an LED, a siren, and/or a buzzer. The device 200 upon detection of an actual fire, triggers the alarm of the device or the fire detection and alarm system to alert about the fire/smoke. The device 200 further includes a power source such as a battery that is within the housing of the device 200 to supply electrical power to the components of the device. Besides, the device 200 may also be electrically connected to a battery of the fire detection and alarm system already installed at the AOI.

In one or more embodiments, the device 200 includes a display panel 210 indicating the status of the device 200. If the source of the smoke (i.e., the burning material) is identified to be in the non-alarming (safe) category, the device 200 does not activate the alarm but is acknowledged as a textual message displayed on the display 210. Further, if the burning material is identified to be in the alarming category, the device 200 activates the alarm 206 so that the occupants of the AOI are alerted to the presence of the fire and the burning/polluting material. The display 210 also acknowledges the identified burning material and any further indication of what the identified burning material or fire source is.

Referring back to FIG. 3, the invention being implemented in an aspirating fire detection device 300 is illustrated. The aspirating device 300 receives the smoke present at an AOI or environment 302 and facilitates the flow of the received smoke through the sensors 102-A, 102-B to enable identification and discrimination of the smoke and the corresponding burning material. The aspirating device 300 includes a central detection unit 304 having a hollow housing 306 enclosing the sensors 102-A, 102-B, which is fluidically connected to a sampling pipe 308. The sampling pipe 308 is exposed to the AOI or environment 302 via a plurality of sampling holes 310 in the sample pipe 308, such that the central detection unit 304 is in fluid communication with the AOI. The central detection unit 304 is in wired and/or wireless communication with the control unit 104. The control unit 104 is also in wired and/or wireless communication with an alarm system 316 and a fire mitigation device 318, both of which are present/installed at a desired location in the AOI or environment 302.

The central detection unit 304 includes an inlet 312 that is connected to the sampling pipe 308. The central detection unit 304 accommodates the device 200 (not shown) or sensors 102-A, 102-B and an outlet 314. Air is aspirated into the central detection unit 304 using an aspirator (not shown), which draws smoke along with the air and pollutants from the AOI/environment 302 through the sampling pipe 308 and into the central detection unit 304 via the inlet 312. The sampled air along with smoke present at the AOI 302 is passed to the first sensors 102-A. The sampled air and smoke are then exhausted from the central detection unit 304 via the outlet 314. The flow of air and smoke through the central detection unit 304 is indicated by the arrows as shown in FIG. 3.

The aspirated air and smoke are allowed to flow into the central detection unit 304 upon the rotation of an impeller of the aspirator. The aspirated air and smoke are then passed to the first sensors 102-A, before being exhausted from the housing via the outlet 314, which allows the first sensors 102-A to detect the concentration of gases present in the received smoke or pollution. Further, the second sensors 102-B are housed in the housing 306 of the central detection unit 304 such that the second sensors 102-B can capture the temporal characteristic of the fire caused by the burning/polluting material in the AOI/environment 302 without any interruption. The control unit 104 identifies and discriminates the smoke and the corresponding burning/polluting material present at the AOI as explained above in detail in FIGS. 1 and 2.

Referring back to FIG. 4, the device 200 or the components of the invention are directly installed at a predefined position in the AOI 402. As illustrated, the first sensors 102-A and the second sensors 102-B are installed at desired positions directly at the AOI 402. The control unit 104 also remains in the same AOI or at a remote location. The sensors 102-A, 102-B may remain in communication with the control unit 104 via wireless media, through a network. Further, the first sensors 102-A and the second sensors 102-B may also remain operatively connected to the control unit 104 via wired media in the same AOI. The control unit 104 is also in wired and/or wireless communication with an alarm system 404 and a fire mitigation device 406, both of which are present/installed at a desired location in the AOI 402.

The first sensors 102-A detect the concentration of gases present in the smoke or pollution present at the AOI. Further, the second sensors 102-B capture the temporal characteristic of the fire caused by the burning material at the AOI. The control unit 104 further identifies and discriminates the smoke and the corresponding burning material present at the AOI as explained above in detail in FIGS. 1 and 2.

In one or more embodiments, when the burning/polluting material is identified to be in the alarming category (real fire), the control unit 104 enables the alarm system 316, 404 of FIGS. 3 and 4 to raise an alarm and further enables the fire mitigation device 318, 406 to mitigate the fire at the AOI 302, 402. In one or more embodiments, the control unit 104 also enables the alarm system 316, 404 to raise an alarm when the concentration of the detected gas in the smoke caused by the burning/polluting material exceeds a first threshold value, and/or a level of the temporal characteristics of the fire caused by the burning material exceeds a second threshold value.

In one or more embodiments, the alarm system 316, 404 includes an aural indicator, such as a siren, LED, buzzer, and the like to alert occupants in the AOI. The fire mitigation device 318, 406 includes one or more fire extinguishers, a sprinkler system, and the like. The alarm system 316, 404 also comprises a display panel indicating the status of the system. If the source of the smoke (burning material) is identified to be a non-alarming source, the generated alarm signal does not activate the aural indicator but is acknowledged as a textual message displayed on the display panel. Further, if the source of the smoke (burning material) is identified to be an alarming fire source, the alarm system activates the aural indicator so that the occupants of the AOI 302, 402 are alerted to the presence of the fire source. The display panel also acknowledges the identified burning material and any further indication of what the identified burning material or fire source is.

Referring to FIG. 5, method 500 for smoke/fire discrimination and identification of the burning material is provided, Method 500 includes step 502 of capturing data pertaining to one or more gas present in smoke caused by a burning material and temporal characteristics of fire caused by the burning material. Method 500 further involves step 504 of identifying the burning material based on the data pertaining to the one or more gas and the data pertaining to temporal characteristics of fire; and triggering a fire event based on the identified burning material.

In one or more embodiment, method 500 includes step 506 of matching the one or more detected gas with a database comprising a set of known gases associated with smoke caused by a plurality of known burning materials, followed by step 508 of matching the captured temporal characteristics with the database comprising a set of known temporal characteristics associated with fire caused by the plurality of known burning materials. Accordingly, the method includes step 510 of identifying and classifying the burning material as one of the known burning materials based on matching of the one or more detected gas and the captured temporal characteristics with the database.

Method 500 further includes step 512 of matching the identified burning material with the database comprising a set of known safe burning materials and a set of known unsafe burning materials and correspondingly discriminating the identified burning material into the safe category or the alarming category. In one or more embodiments, method 500 includes the step of discriminating the identified unsafe burning material into an organic fire source material, a liquid fire source material, and a synthetic fire source material.

In one or more embodiment, method 500 includes the step of identifying the burning material using a temporal model of a machine learning system. The temporal model is configured to determine the burning material based on the temporal characteristics of fire.

Method 500 further includes the step of generating an alarm signal when the burning material is identified to be in the alarming category. In one or more embodiments, the alarm signal can also be generated when a concentration of one or more detected gas exceeds a first threshold value, and/or a level of the captured temporal characteristics exceeds a second threshold value.

In one or more embodiments, method 500 includes the step of capturing multi-dimensional and temporal characteristics of the fire and smoke caused by the burning material, followed by the step of comparing the captured multi-dimensional and temporal characteristics with the database comprising a set of known multi-dimensional and temporal characteristics associated with fire caused by the plurality of known burning materials, and correspondingly identifying and classifying the burning material as one of the known burning materials.

In one or more embodiments, the burning material is identified and classified as one of the known burning materials based on a voting consensus between one or more nodes that can include the smoke sensor, a gas sensor, and a machine learning engine. The detailed operation of the voting consensus-based decision-making has been described above in detail in conjunction with FIG. 2.

While various embodiments of the invention have been elaborated for detecting fire/smoke causing burning materials and reducing false alarm, the teachings of the invention are equally applicable for detecting pollution (environmental and industrial) and pollution causing materials from factories and the likes, as well as reducing false alarm.

Thus, the invention solves the drawbacks, limitations, and shortcomings associated with existing systems and methods, by providing a solution that discriminates between a real (alarming) fire and a non-alarming fire. Besides, the invention also identifies the source of the fire or smoke, which is not possible in existing systems and methods.

While the invention has been described with reference to exemplary embodiments, it will be understood by those skilled in the art that various changes may be made and equivalents may be substituted for elements thereof without departing from the scope of the invention as defined by the appended claims. Modifications may be made to adopt a particular situation or material to the teachings of the invention without departing from the scope thereof. Therefore, it is intended that the invention not be limited to the particular embodiment disclosed, but that the invention includes all embodiments falling within the scope of the invention as defined by the appended claims.

In interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A system for smoke discrimination and identification of fire source, the system comprising:
    a control unit comprising a processor operatively coupled to a memory storing instructions executable by the processor, the control unit configured to:
    receive data pertaining to one or more gas present in smoke generated by a burning material;
    receive data pertaining to temporal characteristics of fire caused by the burning material;
    match the one or more detected gas with a database comprising a set of known gases associated with smoke generated by a plurality of known burning materials;
    match the captured temporal characteristics with the database comprising a set of known temporal characteristics associated with fire caused by the plurality of known burning materials;
    identify and classify the burning material as one of the known burning materials based on the matching of the one or more detected gas and the captured temporal characteristics with the database;
    match the identified burning material with the database comprising a set of known safe burning materials and a set of known unsafe burning materials; and
    discriminate the identified burning material into any of a safe category and an alarming category based on the matching; and
    trigger a fire event based on the identified burning material.

2. The system of claim 1, wherein the control unit is configured to identify the burning material using a temporal model of a machine learning system, wherein the temporal model is configured to determine the burning material based on the temporal characteristics of fire.

3. The system of claim 1, wherein the control unit is configured to discriminate the identified unsafe burning material into any of an organic fire source material, a liquid fire source material, and a synthetic fire source material, based on the matching.

4. The system of claim 1, wherein the system comprises:
    one or more first sensor in communication with the control unit and configured to detect the one or more gas present in the smoke generated by the burning material; and
    one or more second sensor in communication with the control unit and configured to capture the temporal characteristics of fire caused by the burning material.

5. The system of claim 1, wherein the system comprises a multi-type wave sensor in communication with the control unit and configured to capture multi-dimensional and temporal characteristics of the fire and smoke caused by the burning material.

6. The system of claim 5, wherein the control unit is configured to:

match the captured multi-dimensional and temporal characteristics of the fire and smoke with the database comprising a set of known multi-dimensional and temporal characteristics associated with smoke and fire caused by the plurality of known burning materials;
    identify and classify the burning material as one of the known burning materials based on the matching.

7. The system of claim 4, wherein the one or more first sensor comprises one or more gas sensors, and
    wherein the one or more second sensor comprises one or more of photodiode, and temperature sensor.

8. A device for smoke discrimination and identification of fire source, the device comprising:
    one or more first sensor operable to detect one or more gas present in smoke generated by a burning material;
    one or more second sensor operable to capture temporal characteristics of fire caused by the burning material; and
    a control unit operatively coupled to the one or more first sensor and the one or more second sensors, the control unit comprising a processor coupled to a memory storing instructions executable by the processor and configured to:
    receive data pertaining to the one or more detected gas;
    receive data pertaining to the captured temporal characteristics;
    match the one or more detected gas with a database comprising a set of known gases associated with smoke caused by a plurality of known burning materials;
    match the captured temporal characteristics with the database comprising a set of known temporal characteristics associated with fire caused by the plurality of known burning materials;
    identify and classify the burning material as one of the known burning materials based on the matching of the one or more detected gas and the captured temporal characteristics with the database;
    match the identified burning material with the database comprising a set of known safe burning materials and a set of known unsafe burning materials, and
    discriminate the identified burning material as any of a safe category and an alarming category based on the matching; and
    trigger a fire event based on the identified burning material.

9. The device of claim 8, wherein the device comprises an alarm unit operatively coupled to the control unit, wherein the control unit is configured to actuate the alarm unit when the burning material is identified to be in the alarming category.

10. The device of claim 8, wherein the device comprises a multi-type wave sensor operatively coupled to the control unit and configured to capture multi-dimensional and temporal characteristics of the fire and smoke caused by the burning material;
    wherein the control unit is configured to:
    match the captured multi-dimensional and temporal characteristics of the fire and smoke with the database comprising a set of known multi-dimensional and temporal characteristics associated with smoke and fire caused by the plurality of known burning materials; and
    identify and classify the burning material as one of the known burning materials based on the matching.

11. The device of claim 8,
    wherein the device is adapted to be configured within an aspirating fire detection device that is adapted to:
    receive the smoke present at an area of interest (AOI); and facilitate flow of the received smoke through the device to allow the identification and discrimination of the smoke and the corresponding burning material.

12. The device of claim 8, wherein the device is adapted to be installed at predefined positions at an AOI and configured to identify and discriminate the smoke and the corresponding burning material present at the AOI.

13. A method for smoke discrimination and identification of fire source, the method comprising:

capturing data pertaining to one or more gas present in smoke caused by a burning material;

capturing data pertaining to temporal characteristics of fire caused by the burning material;

matching the one or more detected gas with a database comprising a set of known gases associated with smoke caused by a plurality of known burning materials;

matching the captured temporal characteristics with the database comprising a set of known temporal characteristics associated with fire caused by the plurality of known burning materials;

identifying and classifying the burning material as one of the known burning materials based on matching of the one or more detected gas and the captured temporal characteristics with the database;

matching the identified burning material with the database comprising a set of known safe burning materials and a set of known unsafe burning materials, and discriminating the identified burning material into any of the safe category and the alarming category based on the matching; and triggering a fire event based on the identified burning material.

14. The method of claim 13, wherein the method comprises generating an alarm signal when the burning material is identified to be in the alarming category.

15. The method of claim 13, wherein the method comprises generating an alarm signal when a concentration of the one or more detected gas exceeds a first threshold value, and/or a level of the captured temporal characteristics exceeds a second threshold value.

16. The method of claim 13, wherein the method comprises discriminating the identified unsafe burning material into any of an organic fire source material, a liquid fire source material, and a synthetic fire source material.

17. The method of claim 13, wherein the method comprises:

capturing multi-dimensional and temporal characteristics of the fire and smoke caused by the burning material; and comparing the captured multi-dimensional and temporal characteristics with the database comprising a set of known multi-dimensional and temporal characteristics associated with fire caused by the plurality of known burning materials; and identifying and classifying the burning material as one of the known burning materials based on the matching.

* * * * *